United States Patent [19]

Roy-Burman et al.

[11] Patent Number: 5,112,767
[45] Date of Patent: May 12, 1992

[54] VECTORS WITH ENHANCER DOMAINS

[75] Inventors: Pradip Roy-Burman, Monterey Park; David A. Spodick, Newport Beach, both of Calif.

[73] Assignee: University of Southern California, Los Angeles, Calif.

[21] Appl. No.: 164,280

[22] Filed: Mar. 4, 1988

[51] Int. Cl.$^5$ .................. C12N 15/85; C12N 15/67; C12N 15/79; C07H 21/04

[52] U.S. Cl. .................. 435/320.1; 536/27; 435/69.1; 435/172.3; 935/6; 935/8; 935/22; 935/34

[58] Field of Search .............. 435/320, 172.3, 235, 435/320.1; 935/32, 23, 34, 36, 57, 6, 8, 22; 536/27

[56] References Cited

PUBLICATIONS

Spodick, D. A., Jan. 1988, *Dissertation Abstracts*, vol. 48/07-B, p. 1898.
Drescher, B. et al., Sep. 22-25, 1987, *Seventeenth Meeting of the European Tumor Virus Group*, p. 86.
Roach, A., et al., 1984, *Gene*, vol. 32, pp. 389-398.
Niman, H. L., et al., 1980, *Journal of the National Cancer Institute*, vol. 64, No. 3, pp. 587-594.
Reeves, R. H., et al., 1984, *Journal of Virology*, vol. 52, No. 1, pp. 164-171.
Itin, A., et al., 1985, *Journal of Virology*, vol. 54, No. 1, pp. 236-239.
Hess et al., *Science*, 229:482-485 (Aug. 2, 1985).
*Current Communications in Molecular Biology*, Cold Spring Harbor Lab., Gluzman & Shenk (eds.), pp. v-x, 3-5, 103-109 (1983).
Roy-Burman et al., *XIIIth Smposium of the International Association for Comparative Research on Leukemia and Related Diseases*, Jerusalem, Israel (Nov. 8-13, 1987) (Abstract).
Spodick et al., *RNA Tumor Viruses*, p. 203 (May 19-24, 1987) (Abstract).
*RNA Tumor Viruses, Molecular Biology of Tumor Virus, 2/ Supplements and Appendixes*, Weiss et al. (eds.), pp. v,34-36, 92-96 (1985).

*Primary Examiner*—Richard A. Schwartz
*Assistant Examiner*—Mary E. Mosher
*Attorney, Agent, or Firm*—Robbins, Dalgarn, Berliner & Carson

[57] ABSTRACT

A vector and in particular a virus, plasmid or oligonucleotide vector including unique enhancer and promoter domains. The vectors of the invention are derived from a retrovirus or feline endogenous proviral elements. The unique enhancer domains exhibit unique tissue specificity. These vectors are useful in gene therapy or gene transfer techniques.

7 Claims, 11 Drawing Sheets

FIG. 3A (1) Nucleotide sequence comparison of exogenous and endogenous RD-114 5' LTRs

```
              -538
       CCACCCTACC  TTCAACTTTG  TAAACGCCTC  ACTCGCAGAG  CCTGTACTCC  CACTAGCTAA
CRL-3  .........T  ...-G..CC.  GT........  .......G..  .T..C..T..  ...C..T.G.
CR-1

-438                                                              -379 U3
EX-LTR AGCTGTAC--  ..........  ..........  ----- AGG  CTGCTACATA  CATGTTATTA
CRL-3  ........CC  CCACCTTCC.  ..........  CAGGAAC...  T..TC.....  G.|-------
CR-1                                                              A.|

-338                                          |———————————————————————
EX-LTR TGCTAACATA  AA|TAGCCGGA  AAGTCCCCAG  CCGTA|CGCAA  CCCGGGCCCC  GAGTTGCATC
CRL-3  ........-.  G.|....A...  .G......T.  ..........  ..........  ----------
CR-1   ......C...  ..|--A.A...  -G......T.  ..........  ..........  ----------
                                                       DR-A1            DR-B1

Hind III
       -238
EX-LTR |TAGCCGGA   TT-- CCCCGGG   GTAACCCCGT  ACGAAATTAC  CCACAACCCC  AACCACCACC
CRL-3  A.......    ...T..A.-    .G........  ..........  .........T  ..........
CR-1   --A.A...    .......A.    ..........  ..........  ...C.....T  .........T -138
EX-LTR AGAAACTTCA  TTTCCCAAGC  GCGCCAACTC  +1 U3  TTATCGGGGC  TCTCCCGCTT  TCTAACACTG
CRL-3  .........C  ..........  ..........        ..........  ..........  ......C...
CR-1                                              A.........                ......C...
                                                           +1 R -38    TATA Box
EX-LTR CAAAATGG|TA TAAAA|GACCT  GTGGTCTTT   TCATTCCATA  GGGCCTAGGA  GTTGGCTCC
CRL-3  ........A.  .C...|.....  ..........  ..........  ..........  ......C..
CR-1   ........A.  .C...|.....  ..........  .......C..  ..........  ......C..

63
EX-LTR GGAGTGCCGC
CRL-3  .........T
CR-1   .........T
```

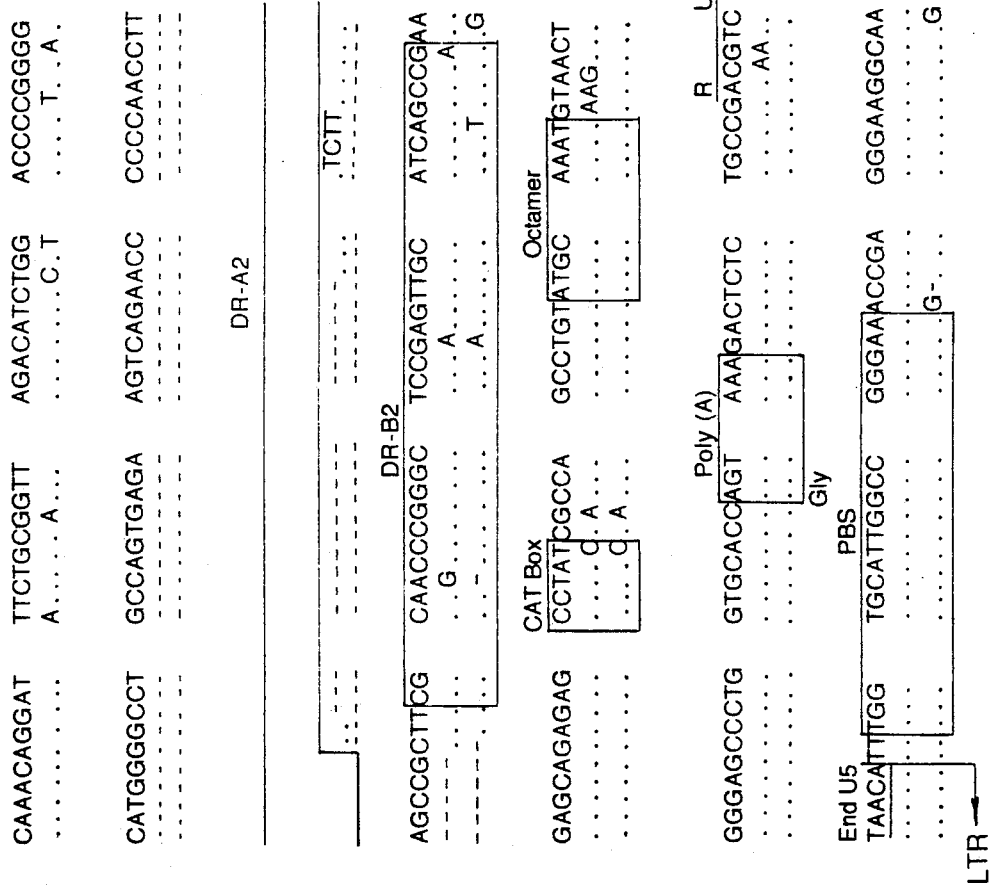
FIG. 3A (2)

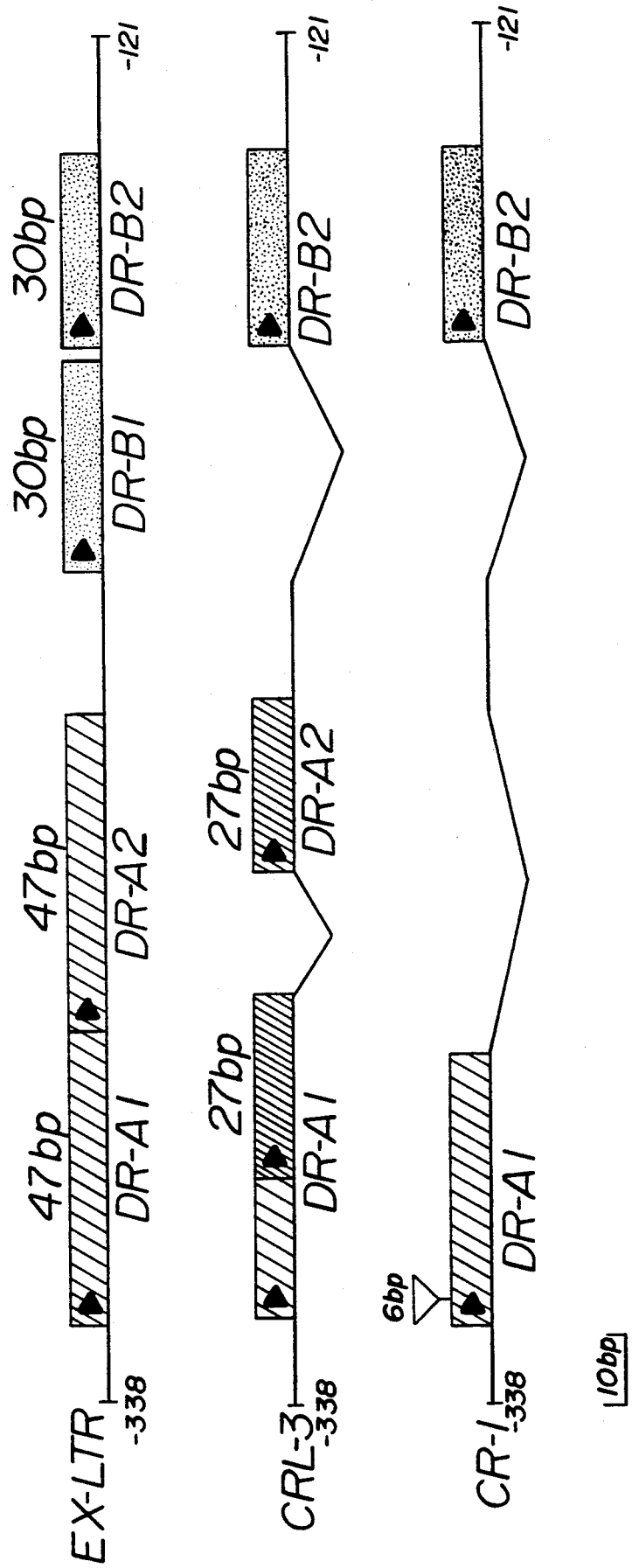
FIG. 3B  SCHEMATIC REPRESENTATION OF DIRECT REPEATS

Sequence comparison of the 47 and 30 bp DRs

```
DR-A1 (EX-LTR)   TAAC------ CGCTT CATTT CGCTT ........ CGCTT CTGTAAAAC CGCTT ATGCGCCCCACCC--
DR-A2 (EX-LTR)   ---------- ..... ..... ..... ........ ..... ......... ..... .............--
DR-A1 (CRL-3)    ---------- ..... .C.C. ..... ........ ..... ..TCTT... ..T.. ....C..A....ATA
DR-A2 (CRL-3)    ---------- ..... ..... ..... ........ ..... ..TCTT... ..T.. ....C..A.....TA
DR-A1 (CR-1)     ...GATGAC. ..... ....C ..... ........ ..... .....CT.. ..CT. ....C..T.....--

DR-B1 (EX-LTR)   CGCAACCCGG GGCCCCGAGTTGCATCAGCCG
DR-B2 (EX-LTR)   .......... ....T................
DR-B2 (CRL-3)    ....G..... ....T..A.............A
DR-B2 (CR-1)     ---.-..... .......A....T........
```

FIG. 3C

FIG. 4 (1)  Sequence comparison of the 5'LTR from RD-114 & BaEV

```
                                                                                              -483                         -379  U3      U3
BaEv                                                                                          AATG                         CATGTTATTA  AAAAGTAAAA

-431
EX-LTR   CGCAGGCAGA  GTTCTTCCA   -----------  AGGCTTGATG  TAGACTCGTT  ACTAAATGAT              ----------                   ----------  ----------
BaEV     ----------  -----------

DR-A1
         -331
EX-LTR   TGCTAACATA  AATAACCGCT  TTCATTTCGC  TTCTGTAAAA                                       CCGCTTATGC                   GCCCCACCCT
BaEV     ----------  -...T..C    ..TG..CT..  ..........                                       .T...TCC                    ...TC.GAA

-231                                                                                                    DR-B1
EX-LTR   CCACCCTAGC  CGGAAAGTCC  CCAGCCGTAC  GCAACCCGGG                                       CCCGAGTTG                    CATCAGCCGC
BaEV     GT.TG...AA  G.TGGC.GGG  ..C.A.CGCT  ......A.A                                        ....AAG....                  ..........G

-131
EX-LTR   TTCATTTCCC  AAGCTTCCCC  GGGACGAAAT  TACCCACAAC                                       CCCAACCACC                   ACCGAGCAGA
BaEV     C.ATCCA..   CCTT.G.GT.  .CC..AAT.GA A..AAG....C.                                      TGGCCT..GAG                  GTTAC..A..AG

-31    TATA BOX                             +1
EX-LTR   GTATAAAGA   CCTGTAACCC  CGTTTATCGG                                                   CTTTCTA---                   ----ACACT
BaEV     C.........  GA....T.G.  .ACAA.....                                                   ..C....CCA                   CATTCCTTAG

U3        R
         70
         |R    U5
EX-LTR   CGTCGGAGTG  CCGCGTGGTT  CTTTGCGCCA  ACTCTCATTC                                       CATAGGGCCT                   AGGAGTTTGG
BaEV     AA.TT.T...  TT.G......  .C.C.....G  ----------                                       ---.ACC..TA                  ....-AC-..
```

FIG. 4(2)

|  |  |  |  |  |  |
|---|---|---|---|---|---|
| CTTTTAGGCC | CTCCCCGTAA | ATGGTTCTGT | TTGTTCGTGG | | |
| CATGGGGCCT | GCCAGTGAGA | AGTCAGAACC | CCCCAACCTT | | |

DR-B2 / DR-A2

```
AACCGCTTTC  ATTTCGCTTC  TGTAAAACCG  CTTATGCGCC
TTGAAAAACA  .GCC.TGCCT  CAGCCCGGAAA  T.CCAAAC..A

CAT BOX                    Octamer
TTCGCAACCC  GGGCTCCGAG  TTGCATCAGC  CGAAAGAAAC
G.A..A.T    .CAT...CCA  GAC.TC..CCG  G.GCTAGC..

Poly (A)
CCAGCCCTGTA  TGCAAATGTA  ACTCAAAATG
AT.........  .......-A.  .GC.T....C.

GGGGA--GCC  CTGGTGCACC                TCTCTGCCGA
A....GG     ..........                .T........

U5                PBS
CTCCTAACAT  TTGGTGCATT  GGCCGGGAA-  ACCGAGGGAA
A.T........  C...G.GC.C  .T........TT  TGA.....--C
```

FIG. 5
HYBRIDIZATION OF OLIGONUCLEOTIDE PROBES
to RD 114 clones
| | 55°C | | 65°C |
|---|---|---|---|
| | PBS$^{Gly}$ | PBS$^{Pro}$ | PBS$^{Gly}$ |
| EX-LTR 1 |  | |  |
| CRI 2 |  | |  |
| CRL3 3 |  | |  |
| CRL3-3' 4 | | | |
| CRL8 5 |  | | |
| CR5 6 |  |  |  |
| CRL17 7 |  | | |
| CR8 8 |  |  |  |
| GA-FeLV 9 | |  | |

FIG. 6
RD-114 mRNA IN T-LYMPOID TUMOR CELL LINES
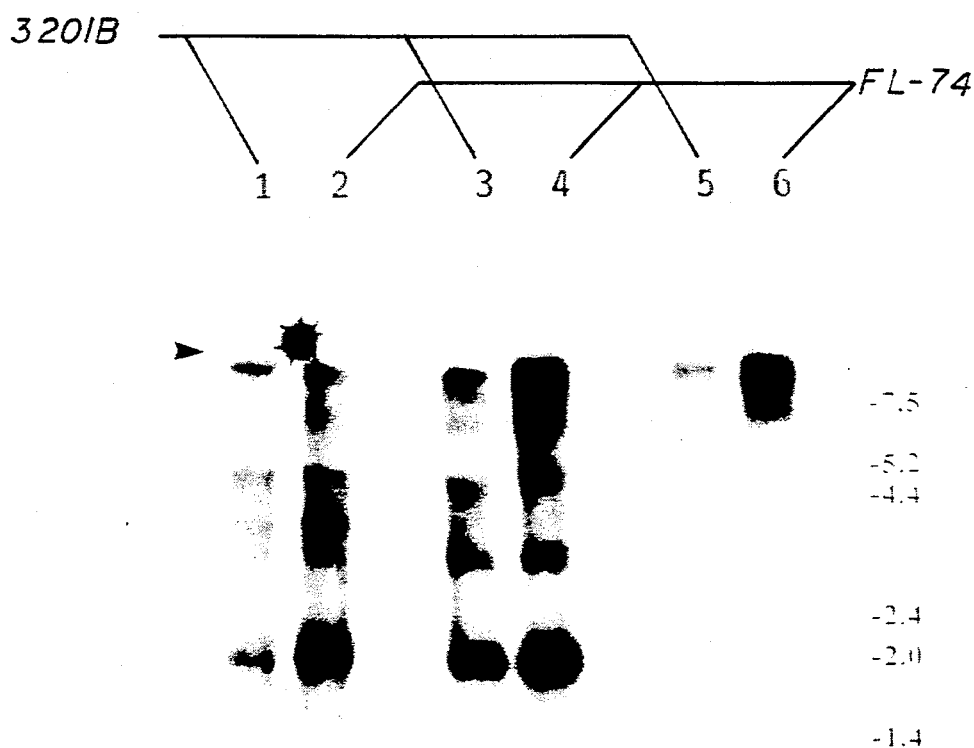
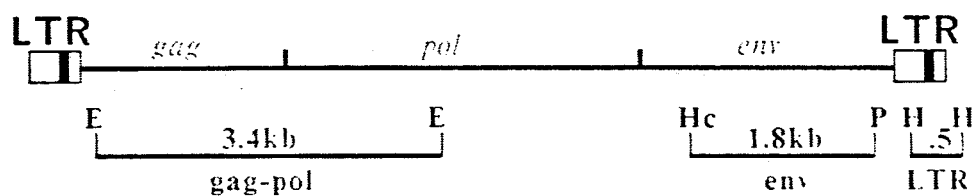

FIG. 7
S1 NUCLEASE PROTECTION ASSAYS
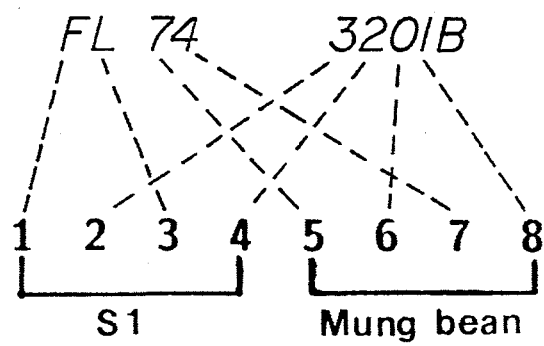
◄ 880bp
◄ 300bp
EX EX EN EN EX EX EN EN
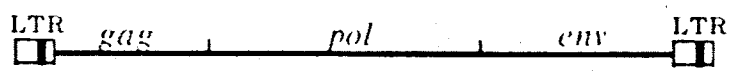
Exogenous
Endogenous

VECTORS WITH ENHANCER DOMAINS

BACKGROUND OF THE INVENTION

The present invention relates to the field of gene therapy or gene transfer techniques in general, and the use of a specifically constructed vector for use in such techniques. In particular, the present invention is directed to vectors constructed to include a virus nucleic acid sequence having unique domains which enhance and promote gene expression in particular tissues. This retrovirus sequence also includes a glycine primer binding site, which is unique among known retroviruses. Primer binding site is the first requirement for retrovirus replication.

Retrovirus and other vectors have found use in various types of applications, e.g. gene therapy. These vectors incorporate specific genes for which expression is desired. The retrovirus of other type of vectors further include various elements which control the expression of such genes. Generally, these other elements include promoter domains, which include specific DNA sequences for the gene expression to begin.

Other elements which control the expression of genes include enhancer domains, which function to enhance the activity of the promotor domain. Typically, the enhancer domain will be operable, that is, facilitate the enhancement of the promotor domain, in only specific tissues. This tissue specificity is a function of the various types of proteins available in particular tissues. In this regard, a specific protein, which may be found in only certain tissues, will bind with the enhancer domain to facilitate the binding of another protein to the promotor domain to initiate gene transcription.

Recently, vectors have been made using the genetic material from retroviruses. These retroviruses include suitable promotor and enhancer domains, which are specific for certain tissues. While many types of such domains are now known, these domains are typically useful for gene therapy with only specific tissue types. It is thus highly desirable to develop other types of vectors which include retrovirus type enhancer and promotor domains useful in other tissue types, or even the same tissue types.

SUMMARY OF THE INVENTION

The present invention is directed at a unique vector, e.g., retrovirus, plasmid or oligonucleotide vectors which incorporates unique tissue specific enhancer domains. These domains include two singular or duplicate unique domains, which are situated upstream from one or more promoter domains. One or more genes for expression can be place downstream of the promoter and enhancer domains.

In particular, a vector of the invention includes single or duplicate DR-A and DR-B domains, which will be described more fully herein. These domains function to enhance a downstream located promoter. The promoter region further includes an octamer region which may also function as a tissue specific enhancer, in that, it interacts with certain proteins found in specific tissue.

The vectors containing DNA sequences of the invention will find use in gene therapy for those target tissues for which the enhancer domains are either specific or highly active or resistant to activation by cellular factors.

BRIEF DESCRIPTION OF THE DRAWINGS

The present invention may be better understood and its advantages will be apparent to those skilled in the art by reference to the accompanying drawings, wherein like reference numerals refer to like elements in the several Figures, and wherein:

FIG. 3 A is an illustration of the nucleotide sequence comparison from plasmid clones incorporating the domains of the invention. The dashes indicate gaps in sequences introduced to maximize homologies, while dots indicate the same base is present.

FIG. 3 B is a schematic representation of the enhancer domain repeats upstream of the HindIII site at −121. Directly repeated units are shown as boxes and shaded either with hatches (DR-A1and −A2) or with stippling (DR-B1 and −B2). The solid arrows represent the start of each repeat unit, and the length of the unit in bp is indicated above the boxes. The 27 bp repeats in CRL-3 are indicated by doubly-dense hatches. FIG. 3C is a sequence comparison of the 47 and 30 bp direct repeats of various plasmid clones. Individual direct repeats from each clone are aligned and shown below the exogenous repeats. Dashes and dots are used to describe sequence differences and similarities as described for FIG. 3 A above.

FIG. 4 is a sequence comparison of the Long Terminal Repeat (LTR) of an exogenous RD-114 retrovirus which includes the relevant domains of the invention and Baboon Endogenous Virus. The 5' LTR sequences are aligned and labeled using the same nomenclature as described in FIG. 3 A. The sequence for BaEV is from Tamura et al. (1981).

FIG. 5 is an illustration of an autoradiogram demonstrating the hybridization of oligonucleotide probes for glycine primer binding site and proline primer binding site to plasmid clones of the invention to determine the presence or absence of such binding site.

FIG. 6 is an illustration of an autoradiogram for the Northern analysis of RD-114-related RNA from two feline T-lymphoid cell lines.

FIG. 7 is an illustration of S1 nuclease protection assays.

DESCRIPTION OF THE INVENTION

Figure 1:
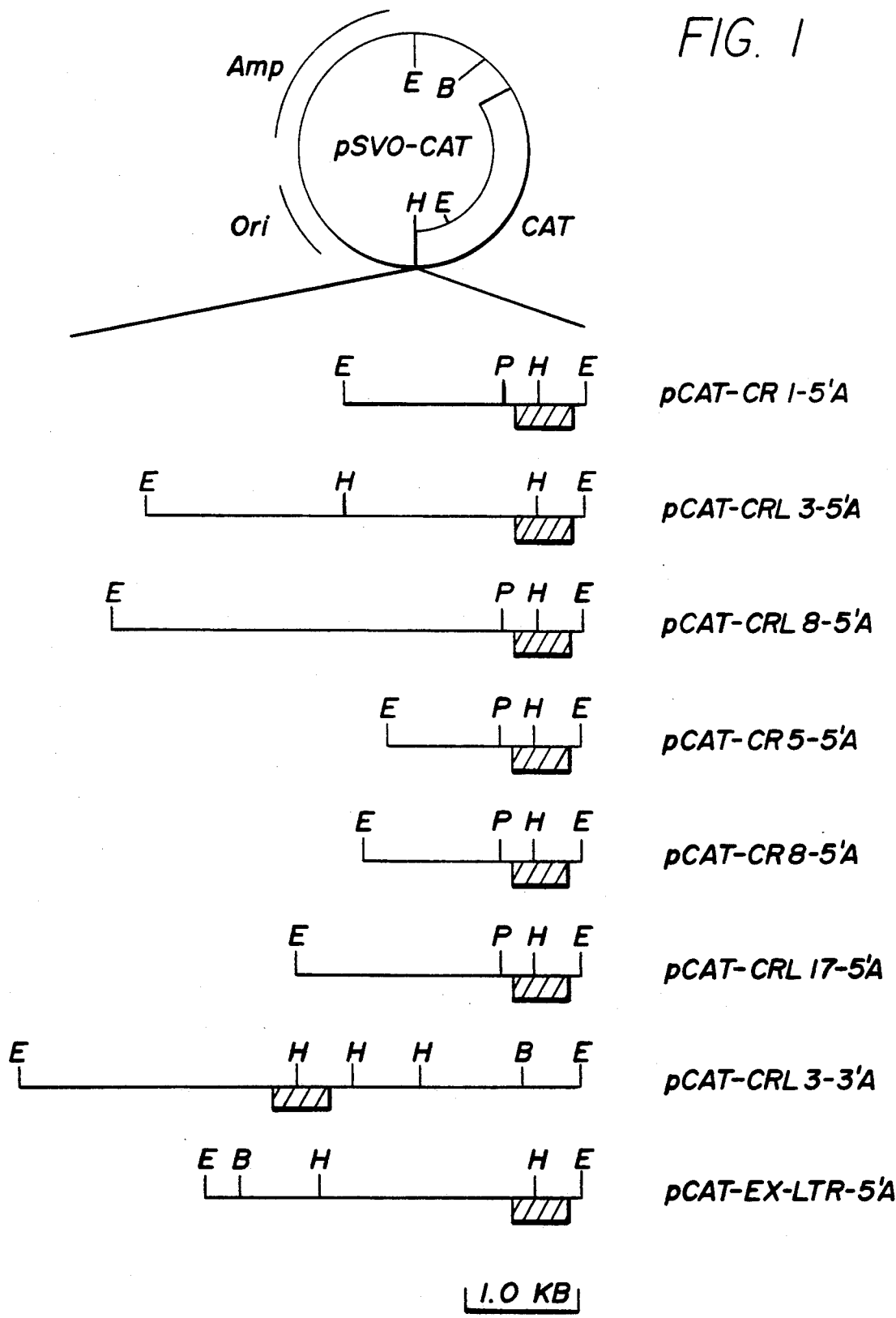
FIG. 1 is an illustration of the construction of a plasmid including the enhancer and promoter domains in accordance with the invention.

The present invention is directed at a novel vector, and in particular a virus, plasmid and oligonucleotide vector which vector includes specific enhancer and promoter domains. These domains may be clones from the long terminal repeat (LTR) portion of a feline endogenous RD-114 proviral loci, or an infectious or exogenous RD-114 provirus.

The sequences which are important and from which the vectors of the invention are constructed, include two singular or replicate enhancer domains tagged as domains DR-A 1 & 2 and DR-B 1 & 2, in FIG. 3 A, which were derived from the exogenous or infectious RD-114 provirus (EX-LTR) and particular feline endogenous RD-114 proviral loci (CRL-3 and CR-1). The exact method and procedures used for deriving the clones plasmid including these particular domains will be described further herein.

In accordance with the general invention vector, and specifically the virus, plasmid or oligonucleotide vector of the invention need only to include a single one of each domain, e.g. either the DR-A1 or —A2 domain, and the DR-B1 or —B2 domain. In this regard, the cloned plasmid labeled CRL-3 and CR-1 include only a single one of the DR-A and DR-B domains, in particular, the DR-A1 and DR-B2 domains, while the cloned plasmid labeled EX-LTR, includes substantial duplicates of each domain. CRL-3 also contains a partial duplication of the DR-A region.

The preferred vectors, and more preferably the virus, plasmid or oligonucleotide vectors of the invention will include those enhancer domains as illustrated in the cloned plasmids labeled in FIG. 3A as EX-LTR or CRL-3, which are the respective domains of the infectious RD-114 provirus (EX-LTR) and a particular feline endogenous RD-114 proviral loci (CRL-3). The most preferred plasmid or oligonucleotide vector will possess replicates of each such domains as does the cloned plasmid labeled EX-LTR in FIG. 3A.

The vector of the invention further include a promoter domain positioned downstream of the enhancer domains. The specific promoter domain includes the CCTAT or CCTAC Box region, the Octamer region and the TATA Box region as seen in FIG. 3A. It should be noted that the various regions of this particular promoter domain are not precisely the same sequence for each of the cloned plasmids illustrated in FIG. 3A, with the sequence of the two cloned plasmid derived from the endogenous proviral loci, CR-1 and CRL-3, possessing a CCTAT or CCTAC and TATA box regions which while the same are different from the respective regions of the cloned plasmid derived from the exogenous or infectious RD-114 provirus, EX-LTR.

It should further be noted that the various enhancer domains need not be positioned adjacent to each other, but may be separated by intervening DNA sequences. Furthermore, the enhancer and promoter domains also need not be positioned at a fixed distance from one another.

The vector of the invention differs from available vectors, and more particularly retrovirus derived vectors, by the above described enhancer domains. In particular, the exact sequences of these enhancer domains incorporated into the vectors of the invention have heretofore not been found in known retrovirus derived vectors, and thus have not been heretofore been incorporated into a virus, plasmid or oligonucleotide vector. Further, the duplication of these enhancer domains has also not been utilized prior to the invention. In this regard, known retrovirus derived vectors, and vectors in general, do not possess such duplicated enhancer domains, and as such, presently available virus plasmid or oligonucleotide vectors do not incorporate these duplicate enhancer domains, as the preferred plasmid, virus and oligonucleotide vectors of the invention.

It is known that enhancer domains in general, are tissue specific. That is, these types of domains will enhance the operation of the promoter domains only in those tissues which include particular proteins that will bind to such domains. Thus, since the enhancer domains of the invention differ from presently available enhancer domains, any vector, and in particular a virus, plasmid or oligonucleotide vector incorporating such domains, which may be specific for tissues other than those targeted by presently available vectors. This unique specificity will allow for the use of the vectors of the invention in gene therapy or gene transfer which presently available vectors are not used.

Another distinction of the vectors of the invention involves the octamer region of the promoter domain. In this regard, octamer regions, and in particular this specific octamer region also present in several human genes, have not been found in the promoter domain of available vectors derived from retroviruses. DNA sequence comparison of the vector of this invention reveals that the only other retrovirus which contains this octamer is Baboon endogenous retrovirus. This particular octamer region is also tissue specific, thus further enhancing the utilization of the vectors of the invention for gene therapy, gene transfer or other genetic manipulations in specific tissues.

A further gene sequence present in a preferred embodiment of the invention is a specific primer binding site located downstream of the enhancer and promoter domains. This primer binding site is a glycine primer binding site. This specific binding site has heretofore not been found in retroviruses. Again, this specific binding site may be tissue specific, and thus be useful in various types of gene therapy for a particular target tissue. It should be noted that the vector of the invention need not include this particular primer binding site, however, such primer binding site will be useful when at least one cycle of replication of the vector is desirable.

The materials used and methods for preparing the plasmid clones which incorporate the above described domains, including the primer binding site, will now be discussed. Furthermore, the procedure and method for confirming the enhanced promotion of gene transcription will also be discussed to demonstrate the usefulness of the described domains as enhancer and promoter domains in gene therapy, gene transfer and related manipulations in vivo or in vitro.

It should be noted in the following discussion that reference to "RD-114" shall mean to include both the exogenous retrovirus and the feline endogenous proviral elements having similarly sequenced Long Terminal Repeats, from which the discussed enhancer and promoter domains were derived. The term "LTR" shall mean this Long Terminal Repeat sequence.

MATERIALS AND METHODS

The plasmid clones were prepared using a test gene desired to be expressed in transfected mammalian cells in culture. This test gene is bacterial chloramphenicol acetyl transferase gene, which will be referred to herein as the CAT gene. The cell lines, H927feline (Rasheed, S. and Gardner, M. B. [1980] Characterization of cat cell cultures for expression of retrovirus, FOCMA and endogenous sarc genes, p. 393–400. In W. D. Hardy, Jr., M. Essex and A. J. McClelland (ed.) Feline Leukemia Virus. Elsevier North Holland, Inc., New York, which is incorporated herein by reference) and NIH/3T3 mouse fibroblast cell lines which were used to assay levels of transient messenger RNA (mRNA), were maintained in Dulbecco modified Eagle medium (DMEM) high glucose, supplemented with 10% fetal bovine serum and antibiotics.

The plasmid clone (pSCle) which contained the Long Terminal Repeat in the upstream position (5' LTR) which was believed to include the discussed domains of an integrated exogenous RD-114 provirus (EX-LTR) was generously provided by R. Reeves (Reeves, R. H. and O'Brien, S. J. [1984] Molecular genetic characterization of the RD 114 gene family of endogenous feline retroviral sequences. J. Virol. 52, 164–171, which is incorporated herein by reference). Restriction maps of six cloned endogenous RD-114 elements which were believed to contain similar LTRs were isolated from a feline placental DNA library (see Soe, L. H., Devi, B. G., Mullins, J. I. and Roy-Burman, P. [1983] Molecular cloning and characterization of endogenous feline leukemia virus sequences from a feline genomic library. *J. Virol.* 46, 829–840, which is incorporated herein by reference) have been reported previously (Spodick, D. A., Soe, L. H. and Roy-Burman, P. [1984] Genetic analysis of the feline RD-114 retrovirus-related endogenous elements. *Virus Research* 1, 543–555). It should, however, be noted that none of these previous researchers mapped or located the enhancer domain sequences as described above.

Selected ones of the LTRs from each of the six endogenous elements, as well as the exogenous 5' LTR, were isolated from EcoRI digested phage or plasmid DNA by gel purification. Each of these LTRs were placed upstream to the CAT gene by blunt-end ligation into the HindIII site of the plasmid pSVO-CAT, which contains the bacterial CAT gene linked to a SV40 polyadenylation signal but without any promoter or enhancer sequences (FIG. 1—for a detailed explanation of this procedure see Gorman, C. M. Moffat, L. F., and Howard, B. H. [1982] Recombinant genomes which express chloramphenicol acetyltranferase in mammalian cells. *Mol. Cell. Biol* 2, 1044–1051, which is incorporated herein by reference).

Recombinant plasmids were isolated which contained the inserted LT fragment either in the correct 5' to 3' direction (relative to the provirus) and designated orientation "A", or the incorrect (inverted) orientation "B". The plasmid pSV2-CAT—which is identical to the pSVO-CAT plasmid except it additionally contains the SV40 early promoter/enhancer region upstream of the CAT gene—was used as a positive control (see again Gorman et al., 1982).

These plasmids were purified by CsCl centrifugation (for a detailed explanation of this procedure see Maniatis, T., Fritsch, E. F., and Sambrook, J. V. [1982] Molecular cloning: a laboratory manual. Cold Spring Harbor Laboratory, Cold Spring Harbor, N.Y., which is also incorporated herein by reference) and the orientations verified by restriction analysis prior to use in transfections.

The transfections and CAT assays were performed as follows:

The previously discussed NIH/3T3 and H927 fibroblast cell lines were used to assay transient levels of mRNA expression by enzymatic CAT activity. On the day before transfection, $5 \times 10^5$ of these cells were plated onto 100 mm dishes in DMEM plus 10% fetal calf serum. Calcium-phosphate DNA precipitates (see Graham, F. L. and Van der Eb, A. J. [1973] A new technique for the assay of human adenovirus 5 DNA. *Virology* 52, 456–467, incorporated herein by reference) were prepared from 40 micrograms (μg of plasmid DNA with 140 μg calf thymus DNA as carrier in 1 ml of HEPES buffered saline (HBS). One-half (20 μg of plasmid DNA) of the precipitate was added to each plate followed four hours later by a four min. glycerol shock (15% glycerol in HBS) (see Parker, B. and Stark, G. R. [1979] Regulation of simian virus 40 transcription: sensitive analysis of the RNA species present early infections by virus or viral DNA. *J. Virol.* 31, 360–369, for a detailed explanation of this procedure, which is incorporated herein by reference). The cells were washed with fresh medium and incubated for 36–48 h at 37° C. The cells were collected by scraping, sonicated and 40 μl of supernatant was incubated for 1 h with 14 C-chloramphenicol as described (see Gorman et al., 1982). Percent conversion of 14 C-chloramphenicol to its acetylated forms was measured by liquid scintillation counting of scraped TLC silica gel plates.

Three LTRs were selected for DNA sequencing analysis. Similar restriction fragments containing each LTR were analyzed using both the "shotgun" (see for more detail Deininger, P. L. [1983] Random subcloning of sonicated DNA: application to shotgun DNA sequence analysis. *Anal. Biochem.* 129, 216–223, which is incorporated herein by reference) and the rapid deletion (see Dale, R. M. K., McClure, B. A., and Houchins, J. P. [1985] Rapid single-stranded cloning strategy for producing a sequential series of overlapping clones for use in DNA sequencing: Application to sequencing the corn mitochondrial 18S rDNA *Plasmid* 13, 31–40, which is incorporated herein by reference) methods for generating overlapping clones. M13 clones representing both DNA strands were sequenced by the dieoxy chain termination method (see Sanger, F., Coulson, A. R., Barrell, B. G., Smith, A. J. H., and Roe, B. A. [1980] Cloning in single-stranded bacteriophage as an aid to rapid DNA sequencing. *J. Mol. Biol.* 143, 161–178, which is incorporated herein by reference). Analysis and alignment of the sequences was aided by the Bionet computer programs. Oligonucleotide hybridizations.

Two 18-mer oligonucleotide probes, corresponding to the 3' ends of proline and glycine tRNAs, were synthesized and end-labelled with T4 polynucleotide kinase and gamma $-^{32}$P-ATP. Nitrocellulose strips which had been spotted with one microgram plasmid DNA and baked for 2h at 80° C. were prehybridized overnight at 65° C. in 6X NET (1X NET is 0.15 M NaCl, 1 mM EDTA, 15 mM Tris-HCl, pH 8.3) 5X Denhardt's solutions, and 0.1% SDS (see for more detail Miyada, C. G. and Wallace, R. B. [1986] Liver-specific expression of a Qa-encoded class I gene is associated with DNA hypomethylation. *Mol. Cell Biol* 6. 315–317, which is incorporated herein by reference). The filters were hybridized in the same solution with $2 \times 10^6$ cpm/ml of labelled probe at 55° C. overnight. Washing was for 5 min. at room temperature in two changes of 6X SSC (0.15 M NaCl, 0.015 M Na Citrate) (low stringency wash) followed by successive two minute washes at 55° C., 60° C. and 65° C. (high stringency washes). Each wash was followed by autoradiography before the blot was subjected to the next higher stringency wash. RNA analysis.

Polyadenylated RNA was electrophoresed on a 1% agarose-2.2M formaldehyde denaturing gel as described (see for more detail Maniatis et al., 1982). The gel was blotted onto Hybond-N nylon filters and hybridized with nick translated probes according to the suppliers instructions (Amersham Corp. Canada Ltd, 505 Iroquois Shore Rd., Oakville, Ontario L6H 2R3, Canada, "Membrane transfer and detection methods", publication for research use only, 1985 which is incorporated herein by reference). Filters were washed twice with 2X SSC, 0.1% SDS, for 30 min. at 65° C. and finally with 0.2X SSC, 0.1% SDS, at room temperature. Autoradiography was at $-70°$ C. with intensifying screens.

Nuclease-SI protection analysis

Single strand specific nuclease protection analysis of polyadenylated RNA using 5'-end labeled probes were performed according to the procedure of Berk and Sharp (Berk, A. J. and Sharp, P. A., [1977], Sizing and mapping of early adenovirus mRNA by gel electrophoresis of $S_1$ endonuclease-digested hybrids. *Cell* 12, 721–732, as modified by Weaver and Weissmann (Weaver, R. F. and Weissmann, C. [1979] Mapping of RNA by a modification of the Berk-Sharp procedure: the 5' termini of 15S beta globin m RNA precursor and mature 10S beta globin mRNA have identical map coordinates. *Nucleic Acids Res.* 7, 1175–1193), both of which references are incorporated herein by reference. Hybridization was carried out at 49° C. and 52° C. and hybrids were digested with 400 units/ml of either nuclease-SI (at 20° C. for 2 h) or Mung Bean nuclease (37° C. for 1 h). Nuclease protected DNA strands were recovered after phenol extraction, precipitated by ethanol, and analyzed on 1.5% agarose gels (Maniatis et al., 1982).

RESULTS

Promoter abilities of RD-114 LTRs

In order to compare the transcription promotion capacity of the various cloned endogenous RD-114 proviral sequences, the ability of individual RD-114 LTR regions to direct transient expression of the CAT gene was tested when transfected into two different cell lines. While the exact 3' borders for LTRs were not determined from restriction mapping in our earlier work, an EcoRI site present just downstream of the 5' LTR was seen to be conserved in all RD-114 elements (see for more detail Spodick et al., 1984). Thus, all 5' LTR-containing fragments used for making CAT expression plasmid had similar structural features except for cellular flanking sequences. These included: various amounts (1 to 3 kb) of upstream flanking DNA; the entire 5' LTR; and 150 bp of downstream sequences up until the conserved EcoRI site (FIG. 1).

A single 3' LTR from one of the cloned endogenous RD-114 provirus elements (CRL3) was also included in the constructions. This LTR, also isolated within an EcoRI fragment, contained 2 kb upstream env and 2 kb downstream flanking DNA sequences in addition to the complete LTR structure. LTR fragments were inserted upstream of the CAT gene of the plasmid pSVO-CAT in both orientations and transfected into either NIH/3T3 mouse fibroblast cell lines or H927 feline cells.

Figure 2:
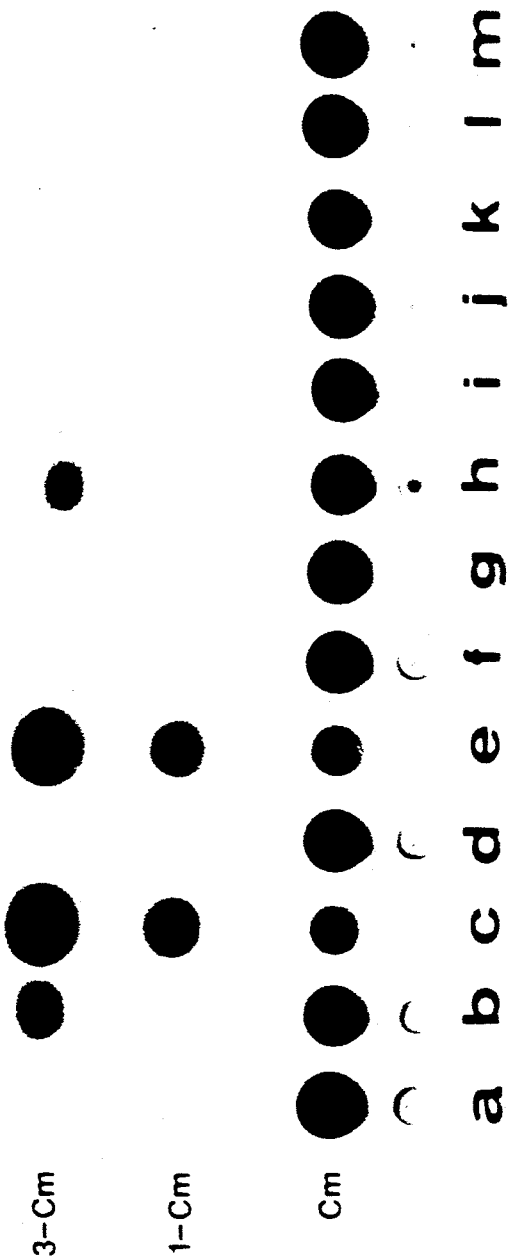
FIG. 2 is an illustration of an autoradiogram for a comparison of the promoter activity of plasmids of the invention in NIH/3T3 mouse cells.

The results of the CAT assay from transfection into NIH/3T3 cells is shown in FIG. 2. Only two of the various plasmid clones having the RD-114 LTRs studied showed promoting activity in mouse NIH/3T3 cells. The plasmid clone possessing the 5' LTR from exogenous RD-114 (EX-LTR) expressed approximately 10 fold higher expression of the CAT gene than the control pSV2-CAT plasmid (FIG. 2, lane c). Of the six endogenous 5' LTRs tested, only one plasmid clone (CRL-3 (FIG. 2, lane e) displayed marked promoter activity, and this was at a level approximately 3 fold higher than that of the control plasmid pSV2-CAT. When the CRL3 plasmid clone was tested in a homologous feline cell line (H927), a significant drop in promoter activity relative to the control pSV2-CAT plasmid was observed (Table 1).

While the absolute level of expression of the control pSV2-CAT plasmid did not vary significantly between the two cell lines (the ratio of pSV2-CAT expression in NIH/3T3 to H927 cells was approximately 0.85), the level of expression achieved by the plasmid clone CRL-3 dropped to one-half the level of pSV2-CAT. Similarly, the EX-LTR plasmid clone also showed reduced activity in H927 feline cells, the reduction being 35% from the level in NIH/3T3 mouse cells. The remaining cloned plasmid LTR did not show any significant activity in either cell line.

The sequences of two endogenous RD-114 LTRs containing plasmid clones derived from the phage clones CRL-3 and CR-1 and those of the cloned plasmid derived from exogenous LTR (EX-LTR) were determined. The sequences of the CRL-3 and CR-1 derived plasmid clones were aligned to obtain maximum conformity to the sequence of the EX-LTR derived plasmid clone (FIG. 3A). The assignment of the functional domains for "TATA" box "CCTAT or CCTAC" box and poly-adenylation signal was based on similarities to reported retroviral LTR consensus sequences (see Weiss, R., Teich, N., Varmus, H. and Coffin, J., (ed.) [1985] *RNA tumor viruses: molecular biology of tumor viruses, Second Edition,* Suppplement and Appendixes. Cold Spring Harbor Laboratory, Cold Spring Harbor, N.Y., which is incorporated herein by reference). This alignment was also made by a comparison with the reported sequence of Baboon endogenous virus (BaEV) (Tamura, T. A., Noda, M. and Takano, T. [1981] Structure of the baboon endogenous virus genome: nucleotide sequences of the long terminal repeat. *Nucleic Acid Res.* 9, 6615–6626, which is incorporated herein by reference) which shows sequence homology to the RD-114 virus (Benveniste, R. E. and Todaro, G. J. [1974] Evolution of C-type viral genes: inheritance of exogenously acquired viral genes. *Nature* [London] 252, 456–459; Benveniste, R. E. and Todary, G. J. [1976] Evolution of type C viral genes: evidence for an Asian origin of man *Nature* [London] 261, 101–108; Cohen, M. Rince, N., Stephens, R., and O'Connell, C. [1982] DNA sequence relationship of the baboon endogenous virus genome to the genomes of other type C and type D retroviruses. *J. Virol* 41, 801–812, which are incorporated herein by reference).

Several different criteria were used for tentatively assigning boundaries of Unique 3' Region (U3), Redundant Terminal Region (R) and Unique 5' Region (U5). Since the LTR of all retroviruses are known to be bound by "TG...CA" inverted repeats (see Temin, H. M. [1981] Structure, variation and synthesis of retrovirus long terminal repeat. *Cell,* 27, 1–3, which is incorporated herein by reference). The upstream pentanucleotide "TGTTA" found at position −379 and the inverted orientation of the downstream pentanucleotide "TGTTA" delineated the beginning and the end of the LTR in the endogenous clone. This downstream end of the LTR was designated as the putative start of U3. The 5' border of U3, however, remains to be confirmed by comparison of 5' and the downstream located 3' LTRs. The nucleotides marking the start of R and the end of U5 were readily apparent from a comparison of the three LTRs to the previously reported sequence of the 5' terminus of RD-114 viral RNA (see Lovinger, G. G. and Schochetman, G. [1980] 5' terminal nucleotide sequences of type C retroviruses: features common to noncoding sequences of eucaryotic messenger RNAs. *Cell* 20, 441–449, which is incorporated herein by reference). The tentative boundary between R and U5 was based on the similarity to a consensus sequence with which U5 region of mammalian retrovirus begins; it should, however, be noted that like BaEV, RD-114 sequences are not highly conserved in this region (see Chen, H. R. and Barker, W. C. [1984] Nucleotide sequences of the retroviral long terminal repeats and their adjacent regions. *Nucleic Acid Res.*, 12, 1767-1778, which is incorporated herein by reference). A high degree of sequence homology was also noted in the R-U5 portion among the various endogenous and exogenous RD-114 LTRs.

Major sequence variations are within U3

The U3 region of LTRs, in general, have been shown to contain the fundamental elements for both transcriptional promotion and enhancement (see Weiss et al., 1985). Each of the three LTRs of the plasmid clone discussed above possessed a consensus "TATA" (Hogness) box sequence at −30 bp from the cap site (FIG. 3A). The CRL-3 plasmid clone contained a base change from T to C at the start of this sequence, but since both CRL-3 and EX-LTR plasmid clones possessed active LTRs, that is an LTR demonstrated as an expression system, this difference is apparently not very significant. No consensus "CAT" box (CCAAT), which is typically present in retroviral LTR promoter domains, was found upstream of the "TATA" box, but by comparison to the reported BaEV sequence (Tamura et al., 1981), a closely related box (CCTAT or CCTAC) was found at position −68 in the three plasmid clone LTRs being examined.

All of the sequence variation among the three plasmid clone LTRs being examined demonstrated in the PBS, U5, R and U3 region from −1 to approximately −180 could possibly be explained by chance point mutations or one bp insertions or deletions. The 5' ends of U3 of these three examined plasmid clone LTRs, however, had diverged substantially from one another. The structural divergence among the three LTRs in the U3 region could be best described by comparing the two endogenous LTRs to the exogenous LTR (FIG. 3B-C).

The plasmid clone exogenous LTR (EX-LTR) contained two sets of tandem direct repeats (labeled by DRs) separated by 23 nucleotides. The first 47 bp DR (DR-A1), was immediately followed by a perfect 47 bp copy (DR-A2). The second, 30 bp DR (DR-B1) was repeated imperfectly (29 of 30 bp) as DR-B2 with three nucleotides in between copies. Relative to plasmid clone EX-LTR, the two endogenous plasmid clone LTRs (CRL-3 and CR-1) contained several deletions of repeated sequences. Plasmid clone CR-1 had only one copy of each of the 47 bp DR (DR-A1, with a six bp insertion and a five bp deletion) and the 30 bp DR (DR-B2, 3 bp changes, one nucleotide shorter). In plasmid clone CRL-3, DR-A1 was highly divergent, while the 5' portion of DR-A2 was deleted resulting in an imperfect (one nucleotide different) DR of 27 nucleotides. Like plasmid clone CR-1, plasmid clone CRL-3 had no copy of the DR-B1 repeat, but homology to the sequence of plasmid clone EX-LTR was reestablished three nucleotides before, and continued through the DR-B2 repeat (4 bp changes).

Within the DR-A1 repeated sequences found in all of the plasmid clone LTRs, there was also a variation in the number of copies of a five base repeated motif, "CGCTT". Plasmid clone EX-LTR contained six perfect copies of this motif, while plasmid clones CRL-3 and CR-1 contained only four and three copies, respectively (FIG. 3C). Comparisons of the nucleotide sequences shown in FIG. 3C also indicated that the two endogenous proviruses, plasmid clones CRL-3 and CR-1, were more closely related to each other than to the exogenous virus plasmid clone EX-LTR. The single nucleotide changes observed in the DR-A1 of plasmid clone CR-1 were infrequently seen in plasmid clone CRL-3. Additionally, the 27 bp region of the DR-A1 and DR-A2 repeats of plasmid clone CRL-3 were more homologous to each other than they were to the corresponding area of the DR-A1 and DR-A2 repeats of plasmid clone EX-LTR.

Beyond 12 nucleotides upstream of DR-A1, there was no significant homology between plasmid clones of EX-LTR and either CRL-3 or CR-1. However, the endogenous plasmid clones, CRL-3 and CR-1, revealed a considerable homology between themselves in this region spanning from −379 to −538 (FIG. 3 A). We speculate that deletions and insertions during the long evolutionary period might have contributed to this major divergence as well as making it difficult to locate the 5'U3 border of the endogenous derived plasmid clone LTRs, CRL-3 and CR-1.

It was also determined that these LTRs contain the immunoglobulin heavy-chain octamer twenty-five nucleotides upstream from the start of the "TATA" box. In each clone there was the conserved octamer sequence "ATGCAAAT" (FIG. 3A). This octameric sequence (or its inversion) has been found and conserved between the "CCTAT or CCTAC" and "TATA" boxes within several genes, most notably the immunoglobulin heavy- (IgH) and light-chain promoters (see Parslow, T. G., Blair, D. L., Murphy, W. J. and Granner, D. K. [1984] Structure of the 5' ends of immunoglobulin genes: a novel conserved sequence. *Proc. Natl. Acad. Sci USA* 81, 2650-2654; Falkner, F. G. and Zachau, H. G. [1984] Correct transcription of an immunoglobulin kappa gene requires an upstream fragment containing conserved sequence elements *Nature*, 310, 71-74, which are incorporated herein by reference). Retention of a nearly intact octamer sequence is necessary for IgH enhancer activity in pre-B cells (see Mason, J. O., Williams, G. T. and Neuberger, M. S. [1985] Transcription cell type specificity is conferred by an immunoglobulin $V_H$ gene promoter that includes a functional consensus sequence. *Cell* 41, 479-487, which is incorporated herein by reference), and protein factors within B-cells have been isolated which specifically bind to this sequence (see Sen, R. and Baltimore, D. [1986] Multiple nuclear factors interact with the immunoglobulin enhancer sequences. *Cell* 46, 705-716, which is incorporated herein by reference). It was interesting to find this octamer sequence conserved within the promoter domains of both the RD-114 derived LTR and the BaEV LTR (FIG. 4), while similar sequences were not observed in other retroviruses including Feline Leukemia Virus and Moloney-Murine Leukemia Virus. By analogy to its function in immunoglobulin genes, this octamer may act in concert with adjacent or upstream DNA sequences within the LTR, and contribute to the tissue-specific expression associated with endogenous RD-114 retroviral sequences.

A putative primer binding site (PBS) was found to reside immediately downstream to the end of the 5' LTR in al three clone LTRs. That is, all three clone LTRs were shown to match 18 of 18 nucleotides in this region (FIG. 3A). A comparison of this region with that of BaEV, the postulated evolutionary progenitor of RD-114, showed that only 12 of 18 nucleotides were homologous (FIG. 4). This site would be bound to by a specific transfer RNA (tRNA).

BaEV, as well most other infectious mammalian oncoviruses (see Chen and Barker, 1984), include PBS to which bind proline tRNA (tRNA$^{Pro}$) to initiate reverse transcription. Mouse mammary tumor virus include PBS to which are bound Lysine 3 tRNA (see Majors, J. E. and Varmus, H. E. [1983] Nucleotide sequencing of an apparent proviral copy of env mRNA defines determinants of expression of the mouse mammary tumor virus env gene. *J. Virol.* 47, 495-504; Peters, G. and Glover, C. [1980] tRNA's and priming of RNA-directed DNA synthesis in mouse mammary tumor virus. *J. Virol.* 35, 31-40, which are incorporated herein by reference) with squirrel monkey retrovirus including PBS to which tRNA bind Lysine 1, 2 (see Chiu, I. M. and Skuntz, S. F. [1986] Nucleotide sequence analysis of squirrel monkey retrovirus reveals a novel primer-binding site for tRNA$^{Lys1,2}$ *J Virol.*, 58, 983-987, which is incorporated herein by reference). Known examples of lentiviruses show recognition for either Lysine 1, 2 tRNA (see Sonigo, P., Alizon, M., Staskus, K., Klatzman, D., Cole, S., Danos, I., Retzel, E., Tiollais, P., Haase, A., and Wain-Hobson, S. [1985] Nucleotide sequence of the visna lentivirus: relationship to the AIDS virus. *Cell* 42, 369-382; Hess, J. L., Pyper, J. M., and Clements, J. E. [1986] Nucleotide sequence and transcriptional activity of the caprine arthritis-encephalitis virus long terminal repeat. *J. Virol.* 60, 385-393, which are incorporated herein by reference) or Lysine 3 tRNA (Stephens, R. M. Casey, J. W. and Rice, N. R. [1986] Equine infectious anemia virus gag and pol genes: relatedness to visna and AIDS virus: nucleotide sequence of the gag-pol region. *J. Virol.* 47, 137-145; Sanchez-Pescadero, R., Power, M. D., Barr, P. J., Steimer, K. S., Stempien, M. M., Brown-Shimer, S. L., Gee, W. W., Renard, A., Randolph, A., Levy, J. A., Dina, D., Luciw, P. A. [1985] Nucleotide sequence and expression of an AIDS-associated retrovirus (ARV-2). *Science* 227, 484-492; Starcich, B., Ratner, L., Josephs, S., Okamoto, T., Gallo, R. C., and Wong-Staal, F. [1985] Characterization of long terminal repeat sequences of HTLV-III. *Science* 227, 538-540; Wain-Hobson, S., Sonigo, P., Danos, 0., Cole, S., and Alizon, M. [1985] Nucleotide sequence of the AIDS virus, LAV. *Cell* 40, 9-17, which are incorporated herein by reference).

Since it was unlikely that the determined PBS of RD-114 would also be bound by proline tRNA (tRNA$^{Pro}$), a literature search was done to find a tRNA species which would be more homologous to the PBS within RD-114. The 3' end of a tRNA isotype of human origin, including a PBS to which glycine tRNA would bind (Gupta, R. C., Roe, B. A., and Randerath, K. [1979] The nucleotide sequence of human tRNA$^{Gly}$ (anticolon GCC). *Nucleic Acid Res.* 7, 959-970, which is incorporated herein by reference), was found to be perfectly complementary (18 of 18 nucleotides) to the RD-114 PBS. We therefore assigned the PBS for the RD-114 virus to correspond to glycine tRNA. This determination is in agreement with an earlier report that glycine tRNA was enriched in a tRNA fraction tightly bound to the infectious RD-114 genomic RNA (Waters. L. C., Mullin, B. C., Bailiff, E. G., and Popp. R. A., [1980] Differential association of transfer RNAs with the genomes of murine, feline and primate retroviruses. *Biochem. Biophys. Acta* 608, 112-126).

In order to determine if most endogenous RSD-114 elements also contained a glycine PBS PBS$^{Gly}$), two different 18-mer oligonucleotides were synthesized corresponding to the last 18 nucleotides of either tRNA$^{Pro}$ or tRNA$^{Gly}$. Duplicate dot-blots of nine different plasmid DNAs, including those plasmids containing LTR derived from RD-114, were hybridized either to tRNA$^{Gly}$ or tRNA$^{Pro}$ oligonucleotide probes and washed at 55° C. (FIG. 5). Only the plasmid clones containing the 5' LTR from an exogenous or six different endogenous RD-114 clones hybridized to the tRNA$^{Gly}$ probe, while the exogenous FeLV 5' LTR was the only clone which hybridized to the tRNA$^{Pro}$ probe after washing at 55° C. [The tRNA$^{Pro}$ probe was also hybridized to an endogenous Feline Leukemia Virus clone, CRE16 (see Soe et al., 1983) (data not shown)].

The 3' LTR from plasmid clone CRL-3 (spot 4) did not hybridize to either probe, and it served as a negative control in this experiment. The oligonucleotide probes used here clearly discriminated between PBS for glycine or proline tRNAs, which had only 12 of 18 nucleotides in common.

To investigate the possibility that some cloned DNAs might contain sequences diverged slightly from the PBS for glycine, the tRNA$^{Gly}$ oligonucleotide probed filter was rewashed at higher temperatures and re-exposed. Little difference was seen after a 60° C. wash (data not shown), but after a 65° C. wash only four of the six endogenous 5' LTRs still hybridized to the probe for tRNA$^{Gly}$. We feel that the stringency was sufficiently high to determine that the four clones which still hybridized to the probe contained 18 of 18 nucleotide matches, while the two clones which hybridized less at 65° C. matched at least 16 of 18 nucleotides (Miyada and Wallace, 1986). It was thus concluded that all six endogenous RD-114 LTR elements studied here contained primer binding sites which could be bound by tRNA$^{Gly}$.

Analysis of RD-114-related transcripts.

Polyadenylated RNA from two different feline T-lymphoid tumor cell lines was examined by Northern analysis. The cell lines were chosen because of their availability in the laboratory and recognizing that RD-14 gene expression was generally elevated in feline lymphomas. When hybridized to an LTR-specific probe, there were at least six prominent species of the RD-114 specific messenger RNA (mRNA) (8.0, 6.5, 4.8, 3.8, 3.2 and 1.9 kb) expressed in both cell lines (FIG. 6, lanes 1 and 2). Five of the six mRNA species contained sequences homologous to the env gene (8.0, 6.5, 4.8, 3.2 and 1.9 kb) (FIG. 6, lanes 3 and 4), while only the highest three molecular weight mRNAs (8.0, 6.5 and 4.8 kb) hybridized the gag-pol probe (FIG. 6, lanes 5 and 6). The band at 3.8 kb hybridized only to the LTR-specific probe and contained no gag-pol or env-related sequences. This transcript could have originated in a solitary LTR or it could represent a transcript originating from or ending in, a proviral LTR but encompassing adjacent cellular gene sequences.

This analysis of steady-state mRNA levels suggested that each of the two cell lines expressed the 8.0 kb, 6.5 and 4.8 kb transcripts which hybridized to all three probes (LTR, gag-pol and env), but were smaller in size compared to the full-length 9.0 kb RD-114 virion RNA (Weiss et al., 1985). Thus it appeared that these mRNA species might be transcripts from three different deleted endogenous RD-14 loci, and might have undergone splicing events to generate env transcripts banding at 3.2 and 1.9 kb. These env transcripts additionally hybridized only to the LTR probe and not the gag-pol probe. Alternatively, some or all of these transcripts could have resulted from abnormal splicing or termination.

To further examine the relationship of the transcripts to the full-length proviral DNA sequence as well as to one of the deleted proviral DNAs (plasmid clone CRL-3) which exhibited significant in vitro transcription promotion activity, we conducted S1 nuclease protection assays on mRNA from two cell lines. The end-labeled probe used was the 3' portion of env plus part of U3 of either the exogenous clone or endogenous CRL-3.

FIG. 7 shows that a 300 bp fragment was protected by the CRL-3 probe, while an 880 bp fragment was protected by the corresponding exogenous (EX-LTR) probe. The same bands were, however, protected in either FL74 or 3201B cell lines. The partial protection results were most likely due to divergences of more than a single nucleotide because single nucleotide mismatches would not be cleaved under the conditions of incubation for S1 nuclease digestion.

In general, the results suggested that there were only stretches of homologous regions between the RNA species expressed and the probes used in our study. It should be noted that the HindIII site which was labeled in these experiments lies well within 200 bp of the beginning of U3. Since the protected fragments from each probe were greater than 200 bp (i.e., 300 bp or 880 bp), the results suggested that the RNA transcripts corresponding to these fragments arose from endogenous proviruses whose LTRs are very likely identical to the CRL-3 and exogenous RD-114 U3 region, respectively.

This data thus demonstrates the existence of the specific LTR sequences, and, in particular, the described enhancer and promoter domains, discussed above, and also demonstrates that such LTRs will initiate transcription useful in gene therapy.

While the preferred embodiment has been described and illustrated, various substitutions and modifications may be made thereto without departing from the scope of the invention. Accordingly, it is to be understood that the present invention has been described by way of illustration and not limitation.

What is claimed is:

1. A constructed vector comprising:
   a promoter domain;
   at least one heterologous structural gene operably linked to said promoter domain; and
   an enhancer domain upstream of said promoter domain and operable to enhance activity of the promoter domain in specific tissues,
   wherein said enhancer domain comprises at least one sequence DR-A selected from the group consisting of
   TAACCGCTTTCATTTCGCTTCT-GTAAAACCGCTTATGCGCCCC ACCC and
   TAACCGCTTTCCTCTCGCTTCT-GTAATCTTGCTTACGCGCCCA ACCA, and
   at least one sequence DR-B selected from the group consisting of
   CGCAACCCGGGCCCCGAGTTGCAT-CAGCCG,
   CGCAACCCGGGCTCCGAGTTGCAT-CAGCCG and
   CGCAGCCCGGGCTCCAAGTTGCAT-CAGCCA.

2. A vector according to claim 1, wherein said enhancer domain further comprises at least one second DR-A sequence TAGTAATCTTGCTTACGCGCC-CCACCC.

3. A vector according to claim 1, wherein said promoter domain comprises a sequence selected from the group consisting of CCTAT and CCTAC.

4. A vector according to claim 1, wherein said promoter domain comprises an octamer of the sequence ATGCAAAT.

5. A vector according to claim 1, wherein said promoter domain comprises a sequence selected from the group consisting of TATAAAA and CATAAAA.

6. A vector according to claim 1, further comprising a glycine primer binding site of the sequence TGGTGCATTGGCCGGGAA.

7. A substantially purifed oligonucleotide consisting essentially of a nucleic acid sequence selected from the group consisting of
TAACCGCTTTCATTTCGCTTCT-GTAAAACCGCTTATGCGCCCCACCC,
TAACCGCTTTCCTCTCGCTTCT-GTAATCTTGCTTACGCGCCCAACCA,
CGCAACCCGGGCCCCGAGTTGCAT-CAGCCG, CGCAACCCGGGCTCCGAGTT-GCATCAGCCG,
CGCAGCCCGGGCTCCAAGTTGCAT-CAGCCA and TAGTAATCTTGCT-TACGCGCCCCACCC.

* * * * *

UNITED STATES PATENT AND TRADEMARK OFFICE
CERTIFICATE OF CORRECTION

PATENT NO. : 5,112,767
DATED : May 12, 1992
INVENTOR(S) : Roy-Burman et al.

It is certified that error appears in the above-identified patent and that said Letters Patent is hereby corrected as shown below:

Title page, should be: VECTORS WITH <u>NOVEL</u> ENHANCER DOMAINS

Col. 1, line 20, delete "of" and insert therefor --or--.

Col. 1, line 54, delete "place" and insert therefor --placed--.

Col. 5, line 53, delete "5 X 105" and insert therefor --5 X $10^5$--.

Col. 8, line 38, delete "Todary" and insert therefor --Todaro--.

Col. 8, line 41, delete "Rince" and insert therefor --Rice--.

Col. 11, line 25, delete "Danos, I." and insert therefor --Danos, O.--.

Signed and Sealed this

Fourteenth Day of September, 1993

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,112,767
DATED : May 12, 1992
INVENTOR(S) : Pradip Roy-Burman, et al.

It is certified that error appears in the above-identified patent and that said Letters Patent is hereby corrected as shown below:

Column 1, line 5, insert the following:

--This invention was made with government support under Contract No. CA-40590 awarded by the National Institutes of Health. The government has certain rights in the invention.--

Signed and Sealed this

Twenty-ninth Day of June, 1999

Attest:

Q. TODD DICKINSON

*Attesting Officer*  *Acting Commissioner of Patents and Trademarks*